US011426629B2

(12) United States Patent
Thomas et al.

(10) Patent No.: US 11,426,629 B2
(45) Date of Patent: Aug. 30, 2022

(54) METHOD FOR QUANTIFYING A SPORTING ACTIVITY

(71) Applicant: COMMISSARIAT A L'ENERGIE ATOMIQUE ET AUX ENERGIES ALTERNATIVES, Paris (FR)

(72) Inventors: Olivier Thomas, Revel (FR); Sebastien Brulais, Saint Laurent du Pont (FR); Herve Dang, Villard Bonnot (FR); Laurent Freytrich, Ivry sur Seine (FR); Jean-Philippe Gros, Le Fontanil Cornillon (FR); Jerome Paulet, Valence (FR); Prince Arnaud Ramahefa-Andry, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 16/756,534

(22) PCT Filed: Oct. 19, 2018

(86) PCT No.: PCT/EP2018/078759
§ 371 (c)(1),
(2) Date: Apr. 16, 2020

(87) PCT Pub. No.: WO2019/077130
PCT Pub. Date: Apr. 25, 2019

(65) Prior Publication Data
US 2020/0324167 A1    Oct. 15, 2020

(30) Foreign Application Priority Data

Oct. 19, 2017 (FR) ...................................... 1759833

(51) Int. Cl.
*G06F 15/00* (2006.01)
*G06F 11/30* (2006.01)
(Continued)

(52) U.S. Cl.
CPC ...... *A63B 24/0062* (2013.01); *A63B 71/0622* (2013.01); *A63B 71/0686* (2013.01);
(Continued)

(58) Field of Classification Search
CPC .................................................. A63B 24/0062
See application file for complete search history.

(56) References Cited

U.S. PATENT DOCUMENTS 6,669,600 B2 * 12/2003 Warner .............. A63B 24/0021
482/4
8,790,220 B2 * 7/2014 Karvonen .......... A63B 24/0062
482/8

(Continued)

FOREIGN PATENT DOCUMENTS

WO    WO 2008/030484 A2    3/2008

OTHER PUBLICATIONS

International Search Report dated Jan. 21, 2019 in PCT/EP2018/078759 filed on Oct. 19, 2018, citing documents AA-AF and AO therein, 3 pages.

*Primary Examiner* — Alvin A Hunter
(74) *Attorney, Agent, or Firm* — Oblon, McClelland, Maier & Neustadt, L.L.P.

(57) ABSTRACT

The invention relates to field of connected sport and specifically a method for quantifying sporting activity implemented by a communication system including: a proximity beacon associated with sports equipment, measuring equipment and a communication node, the method including: (a) communicating between the measuring equipment and the beacon in order to recover a first data packet comprising an
(Continued)

identifier relating to a sporting activity associated with the sports equipment; (b) transmitting, to the node, a second data packet comprising the identifier; (c) at the node, determining parameterisation data of the measuring equipment according to the identifier; (d) transmitting, to the measuring equipment, a third data packet 230 comprising said parameterisation data; and (e) at the parameterised measuring equipment, quantifying the sporting activity.

19 Claims, 3 Drawing Sheets

(51) Int. Cl.
  *A63B 24/00* (2006.01)
  *A63B 71/06* (2006.01)
(52) U.S. Cl.
  CPC ............... *A63B 2071/0625* (2013.01); *A63B 2071/0694* (2013.01); *A63B 2220/30* (2013.01); *A63B 2220/44* (2013.01); *A63B 2220/833* (2013.01); *A63B 2225/54* (2013.01)

(56) References Cited

U.S. PATENT DOCUMENTS

| | | | |
|---|---|---|---|
| 9,008,973 B2* | 4/2015 | French | A63B 24/0087 |
| | | | 702/19 |
| 9,149,223 B2* | 10/2015 | Spears | A61B 5/22 |
| 9,308,417 B2* | 4/2016 | Grundy | A63B 21/4035 |
| 9,403,060 B2* | 8/2016 | Molyneux | A63B 24/0062 |
| 9,808,701 B2* | 11/2017 | Oleson | A43B 3/0005 |
| 2008/0090703 A1* | 4/2008 | Rosenberg | A63B 24/00 |
| | | | 482/8 |
| 2009/0048044 A1 | 2/2009 | Oleson et al. | |
| 2010/0259407 A1 | 10/2010 | Tilvis et al. | |
| 2013/0173033 A1 | 7/2013 | Oleson et al. | |
| 2013/0297669 A1* | 11/2013 | Wang | G16H 50/20 |
| | | | 709/201 |
| 2016/0082317 A1* | 3/2016 | Doherty | G16H 40/67 |
| | | | 340/870.07 |
| 2016/0213977 A1 | 7/2016 | Oleson et al. | |
| 2016/0243403 A1 | 8/2016 | Oleson et al. | |
| 2016/0245840 A1 | 8/2016 | Oleson et al. | |

* cited by examiner

METHOD FOR QUANTIFYING A SPORTING ACTIVITY

TECHNICAL FIELD OF THE INVENTION

The invention relates to the field of connected sport and more particularly the field of methods for quantifying a sporting activity. It finds particularly advantageous applications when it is deployed in sports halls and other sports complexes that accommodate an ever increasing number of sportspersons. The invention is however not limited in its use to this type of environment. This is because it applies also to sports that are practised outdoors, called outdoor sports. More generally, it makes it possible to aggregate quantifications of all sporting activities with each other wherever they are practised.

PRIOR ART

Whereas the number of sportspersons throughout the world is continually increasing and new sporting activities are continuously emerging, new trends are observed in sporting behaviours. In particular, whatever their level, more and more sportspersons are wishing to be able to quantify their sports performances.

For this purpose, there exist several methods for quantifying a sporting activity.

There exist in particular digital platforms using a mobile application on a smartphone and Website. The application integrates algorithms for quantifying the sporting activity of a user by taking advantage of sensors, in particular GPS, integrated in the smartphone or in a smart watch that communicates with the smartphone. The website enables each user to follow his sporting activities and to share his performances with other users of the platform. One problem with this type of platform is that it is not capable of identifying the sporting activity that it is to quantify and therefore requires the user to enter it, usually by making a choice between a pre-established list that is still at the present time limited.

There also exists equipment for measuring sporting activity capable of recognising certain sporting activities. Algorithms have thus been developed that make it possible to detect the transition from swimming to cycling, and then racing, during a triathlon for example, by monitoring certain parameters measured by measuring equipment worn by the user such as a smart watch. In advance, the user will nevertheless have indicated, typically by an interface comprising a scroll-down menu, that the activity relates to a triathlon. These detection algorithms are limited to the identification of predefined sporting activities and/or to concatenations of predefined sporting activities.

In practice, it turns out that the existing solutions for quantifying sporting activity are relatively imprecise.

One object of the present invention is to propose a method for quantifying sporting activity that makes it possible to overcome one or more of the drawbacks of the known methods.

More particularly, one object of the present invention is to propose a method for quantifying sporting activity that makes it possible to improve the quantification of the sporting activity, without significantly making the actions that the user must take more complex.

SUMMARY OF THE INVENTION

To achieve this objective, according to one embodiment, the present invention provides a method for quantifying at least one sporting activity that is implemented by a communication system comprising at least: a proximity beacon carried by sports equipment, at least one measuring equipment intended to be worn by a user and configured to quantify at least one sporting activity of a user, and a communication node. The method comprises the following steps:

Communicating between the measuring equipment and the proximity beacon, preferably in accordance with a near-field communication technique, so as to recover, at at least one from among the measuring equipment and the proximity beacon, a first data packet comprising at least one from among an identifier relating to a sporting activity associated with the sports equipment and an identifier of the measuring equipment;

Transmitting, from at least one from among the measuring equipment and the proximity beacon, to the communication node, a second data packet comprising at least the identifier relating to the sporting activity and the identifier of the measuring equipment;

At the communication node, recovering parameterisation data of the measuring equipment at least according to the identifier relating to the sporting activity, or even according to the identifier of the measuring equipment;

Transmitting, from the communication node to the measuring equipment, a third data packet comprising at least said parameterisation data; and At the measuring equipment, parameterising the measuring equipment according to said parameterisation data and quantifying the sporting activity of the user of the measuring equipment parameterised according to said parameterisation data.

There is thus proposed a digital platform using equipment for measuring sporting activity that is self-contained and simplified, and more particularly not requiring a complex man-machine interface or even not requiring any man-machine interface at the measuring equipment. The cost of the latter is advantageously reduced thereby, which makes the platform more suited to deployment aimed at the general public, and in particular the ever more numerous users of sports halls.

The parameterising of the measuring equipment according to the sporting activity that the user wishes to practice requires, on the part of the user, only getting sufficiently close to the proximity beacon to automatically transmit the identifier relating to the sporting activity associated with the sports equipment at the communication node. The parameterising continues without any further action on the part of the user, in complete autonomy.

The method according to the invention thus improves the quantification of a sporting activity by making the identification of the sporting activity both immediate, preferably prior to the practice thereof, and easy, or even transparent, for the user.

This advantage procured by the invention is therefore particularly appreciated by users who are not familiar with connected sports objects, the latter generally being relatively complex to manipulate.

This simplicity of use will also be appreciated by regular sportspersons. This is because, for the same sporting activity, it is in general necessary to select several data. For example, in order to quantify an activity of swimming in a swimming pool, it is necessary to select the following data: through scroll-down menu interfaces: swimming/stroke in swimming pool/length of swimming pool/type of stroke. Moreover, some sporting activities are grouped together in the same selectable mode as such without allowing this selection of a specific sporting activity. Thus the "fitness" mode may group together numerous physical activities, such as "step aerobics", "low-impact aerobics", "high-impact aerobics", stretching exercises, "squats", etc. There also, the present invention makes it possible to improve the quantification of a sporting activity in that it makes it possible to identify each sporting activity separately or to identify, in a group of sporting activities, the one that will be practised next.

Thus, because of the low cost of the measuring equipment and its simplicity of use, the invention proves to be particularly advantageous for sports clubs, halls or complexes that wish to make measuring equipment available to their clients, for example carried by bracelets.

Furthermore, the method according to the invention does not require developing further movement recognition algorithms that are already complex, in order to identify the sporting activity being practised. More particularly, it does not require developing a generic algorithm for covering a set of activities. The solution on the contrary makes it possible to segment the quantification activity by activity and to use dedicated algorithms for each of the activities, with a high if not absolute degree of recognition.

This is because the identification of the sporting activity followed by the automatic parameterising of the measuring equipment makes it possible to make and interpret measurements in a way that is specific to the activity identified. The invention thus considerably improves the precision of the quantification of the sporting activity.

For example, the same upward movement of the wrist will not be interpreted in the same way if the sporting activity is racing or boxing. In the case of racing, it will be unused or will be merged with other data for precisely calculating the instantaneous speed of the runner, in the case of boxing it will be interpreted as an uppercut.

The method according to the invention therefore helps to increase the quality of the experience offered to the users compared with the existing sporting-activity quantification devices.

According to a variant of the first aspect thereof, the present invention relates to a method for quantifying a sporting activity, the method being implemented by a communication system comprising at least: a proximity beacon carried by a sports equipment, a measuring equipment intended to be worn by a user, the measuring equipment being configured to quantify at least one sporting activity of a user, and a communication node, the method comprising the following steps:

Registering, at the communication node, an association between the measuring equipment and a user profile;

Communicating between the measuring equipment and the proximity beacon so as to recover a first data packet comprising at least one from among an identifier relating to a sporting activity associated with the sports equipment and an identifier of the measuring equipment;

Transmitting, from at least one from among the measuring equipment and the proximity beacon, to the communication node, a second data packet comprising at least the identifier relating to the sporting activity and the identifier of the measuring equipment;

At the communication node, recovering parameterisation data of the measuring equipment at least according to the identifier relating to the sporting activity and, optionally, the user profile;

Transmitting, from the communication node to the measuring equipment, a third data packet comprising at least said parameterisation data; and At the measuring equipment, parameterising the measuring equipment according to said parameterisation data and quantifying the sporting activity of the user of the measuring equipment parameterised according to said parameterisation data.

The method according to this variant thus makes it possible to take into account data relating to the user and entered in his profile, such as for example his level of practice of the sporting activity (beginner, amateur, professional), his size, his weight and other physical parameters, in order to be able to take into account at least one of these data in order to process the measurement data from the sensors. Thus the level of requirement for validating and counting a movement captured can be adjusted differently according to the data relating to the user and entered in his profile. For example, the requirement level for validating and counting an uppercut captured will be higher if the user is a boxing professional or a beginner. For example, a requirement for amplitude of the movement captured can be reduced for a small user in comparison with a larger user.

Another aspect of the present invention relates to a computer program product comprising instructions which, when they are executed by at least one processor, implement the method for quantifying a sporting activity as introduced above.

According to another aspect, the present invention relates to a non-transient medium that can be read by a computer, comprising instructions which, when they are executed by at least one processor, implement the method for quantifying a sporting activity as introduced above.

BRIEF DESCRIPTION OF THE FIGURES

The aims, objects, features and advantages of the invention will emerge more clearly from the detailed description of embodiments thereof that are illustrated by the following accompanying drawings, wherein.

The drawings are given by way of examples and are not limitative of the invention. They constitute schematic outline representations intended to facilitate understanding of the invention and are not necessarily to the scale of practical applications.

DETAILED DESCRIPTION OF THE INVENTION

Before beginning a detailed review of embodiments of the invention, optional features, which may optionally be used in association or alternatively, are stated below:

the step consisting of communicating between the measuring equipment and the proximity beacon comprises:

putting the measuring equipment and the proximity beacon in proximity to one another, and
the proximity beacon being passive:
a reading by the measuring equipment, in accordance with a near-field communication technique, of data stored in the beacon, including at least the identifier relating to the sporting activity, and
the transmission, from the measuring equipment to the communication node, of the first data packet.
Thus a requirement for a modulatable proximity between the beacon and the measuring equipment for the automatic communication of data therebetween makes it possible to reduce, or even to prevent, the risk of occurrence of a communication of this type that would be not intentional but fortuitous;
at least one from among a plurality of measuring equipment, preferably a single measuring equipment from among the plurality, communicates with the proximity beacon. The communication node furthermore recovers parameterisation data from each of the other measuring equipment in the plurality and furthermore transmits, to each of the other measuring equipment in the plurality, a third data packet comprising at least parameterisation data of this equipment. Where applicable, the parameterisation data of each of the other measuring equipment are furthermore recovered according to an identifier of this measuring equipment. Each measuring equipment being associated with a unique identifier, the identifier of each of said other measuring equipment can be recovered by the communication node according to an identifier of the measuring equipment that communicated with the proximity beacon. The identifier of each of said other measuring equipment was for example transmitted, from the measuring equipment that communicated with the proximity beacon, to the communication node, in the second data packet.
The method thus makes it possible to manage the parameterising of a plurality of measuring equipment, this plurality being able in particular to be necessary to the quantification of the sporting activity of a single user and/or to that or those of a plurality of users. The parameterising may be the same or differ from one measuring equipment to another at least according to the identifier of the measuring equipment, or even also according to the identifier relating to the sporting activity.
Thus the present invention proposes a solution that is particularly effective, inexpensive and simple to use for quantifying a sporting activity, suitable for wearing by a user of a plurality of measuring equipment and/or suitable for a sporting activity practised by a plurality of users;
the method may further comprise, before the step of communication between the measuring equipment and the proximity beacon, at the communication node:
Registering, by associating them, the identifier of the measuring equipment and user data, for example issuing from a user profile entered;
the method further comprises, before the step of communication between the measuring equipment and the proximity beacon, at said communication node:
Registering, by associating them, the identifiers of the measuring equipment forming part of the same plurality associated with one from among a user and a plurality of users intended to practice the same sporting activity. Where applicable, the registration also comprises the association of the identifier of each measuring equipment in the plurality with at least one from among a mode of integration of the measuring equipment and a mode of wearing the measuring equipment.

"Mode of integration" means a mode according to which a measuring equipment is integrated in a sporting-activity accessory (for example in a boxing glove, in an oversock, in a helmet, etc.). "Mode of wearing" is a mode according to which a measuring equipment is worn or is intended to be worn by a user, and more specifically by a specific part of the body of the user (for example on the wrist, on the waist, on the ankle, etc.).

For example, the sports equipment is or comprises a sports hall and the beacon can then be carried by a terminal in the sports hall, and more particularly placed on the floor of the sports hall or carried by a wall of the sports hall.

The proximity beacon may be reprogrammable so that the identifier relating to the sporting activity that is associated therewith can vary, for example according to a schedule for occupation of the sports hall, according to a pre-established training program or according to a change of equipment.

The method may apply to a plurality of measuring equipment. In this case, the method may provide for associating several measuring equipment with each other.

The method may also associate each measuring equipment with a user, and more particularly with a user profile.

In a preferred embodiment, the method also associates each measuring equipment with a user, and more particularly with a user profile. At the end of the method, or when the measurement data are processed, the configuration of the measuring equipment thus makes it possible to take into account characteristics related to the profile of the user (the level in the discipline practised, but also the physical parameters of the user).

The method may also associate each measuring equipment with a mode of integration and/or wearing.

In this way, the communication node may in particular recover parameterisation data for each measuring equipment while taking into account any specificities of the user (for example his registration history, his physical parameters (size, weight, age, his level of practice, etc.), the mode of integration of the measuring equipment and the mode of wearing the measuring equipment. Moreover, this registration step allows subsequent aggregation of quantification data obtained that are coherent through the taking into account of the various associations registered between measuring equipment and user or users (and in particular the user data entered in his profile);

a unique identifier associated with each measuring equipment. Thus each identifier uniquely identifies an measuring equipment. As an alternative, a plurality of measuring equipment may be associated with the same identifier. For example, each user in a group practising the squat wears on the wrist a measuring equipment the identifier of which is the same as that of the other users in the group.

the communication system comprises a plurality of communication nodes distributed spatially so as to form a local network (or LAN, standing for local area network). At least one communication node in the plurality is where applicable configured to communicate in accordance with a long-range communication technique, for example with at least one from among a remote database and another local area network formed by another plurality of communication nodes included in the communication system.

The method is thus particularly suited to use by a communication system deployed in a sports hall, or even in a sporting complex, able to accommodate at the same time a large number of users each wearing one or more measuring equipment and practising various sporting activities. Where applicable, a plurality of sports halls or sporting complexes distant from each other and potentially using a local area network as introduced above may be connected together via a long-range communication to make it possible to offer an enhanced experience to a larger number of users;

the measuring equipment comprises a plurality of sensors and the parameterising of the measuring equipment according to the parameterisation data comprises at least the activation or deactivation of at least one sensor in said plurality.

The method thus makes it possible to control the electrical energy consumption of the measuring equipment, in particular so as to increase the autonomy thereof;

the measuring equipment comprises at least one accelerometer, preferably triaxial, and where applicable at least one from among a gyroscope, preferably triaxial, and a magnetometer, preferably triaxial. The quantification of the sporting activity may comprise at least one step of measuring at least one from the following quantities: an acceleration, a speed, an amplitude of movement, a number of turns per minute, a number of movements per minute, a number of repetitions of movement(s) and a type of movement.

the method may further comprise, for example following or during the quantification of the sporting activity, the transmission, from each measuring equipment to at least one communication node, of a fourth data packet comprising data for quantifying the sporting activity.

The method thus makes it possible to aggregate, at the communication node, the quantification data issuing from each measuring equipment;

according to previous feature, said at least one communication node comprises a mobile telecommunication device, such as a smartphone, and the transmission of the fourth data packet comprises the transmission from said mobile communication device to at least one from among another communication node and a distant database.

Thus the method is not limited in its implementation by the extent of the coverage area of one or more fixed communication nodes. The aggregation of the quantification data of the sporting activity may take into account firstly data acquires in sports halls, and secondly data acquired during sporting activities out of doors;

each measuring apparatus is synchronised with a clock of a communication node. This makes it possible to identify when the measurements have been made for real-time applications;

the communication system further comprising at least one communication device, chosen from at least one audio communication device, one visual communication device and one audiovisual communication device, for communicating an information content generated by the communication node for example according to an identifier relating to the sporting activity, the method may further comprise the communication of said information content to at least one user via said at least one communication device.

The method thus makes it possible to communicate to each user or to each group of users any information content useful to the practice of a physical activity, for example the communication of:

instructions or orders, such as the expected mode of wearing of the measuring equipment or such as objectives to be achieved, illustrations, or even monitoring, of a physical performance or of a biological constant of the user, for example according to the quantification data of the sporting activity transmitted to the communication node, recommendations or advice, such as the next sporting activity recommended or such as virtual demonstrations of use of the sports equipment, encouragements, etc.

"Sports equipment" means an instrument by means of which the practice of a sporting activity is obtained: sports or fitness hall, indoor bicycle, rowing machine, running treadmill, body-building apparatus, floor mat, swimming pool, etc.

"Proximity beacon" means a radio device, for example fixed, for short-distance telecommunication.

"Carried by" means, speaking of the relationship of a proximity beacon with a sports equipment that means the fact that the proximity beacon and the sports equipment are associated together physically; the beacon is for example fixed to, or alongside, an indoor bicycle, a rowing machine, a running treadmill, a body-building apparatus, a floor mat or a console situated in a sports hall, etc., as sports equipment 2. The fixing may be direct or indirect; in the second case, the beacon may for example be fixed to an appendage or a cable connected to the sports equipment. Preferably, the fixing is removable.

"Data packet" means any form of digital and/or analogue expression comprising at least one data item and being interpretable.

"A near-field communication" means a communication the radio-frequency range of which does not exceed one metre, and is preferably no more than a few centimetres.

"A long-range communication" means a communication operated by a system that uses a satellite relay, a data link, a high frequency and/or another approved communication system that potentially extends beyond the line of sight, for example a communication operated by at least one system from among systems of the LoRa, Sigfox, GSM, switched telephone network, Internet, etc. type.

"Distant database" means a database that is not embedded in an equipment from which it is indicated as being distant. Thus the distant database is not embedded in a communication node but is situated outside this communication node. The distance between the distant database and the communication node from which the database is distant may for example vary from a few centimetres to thousands of kilometres.

Figure 1:
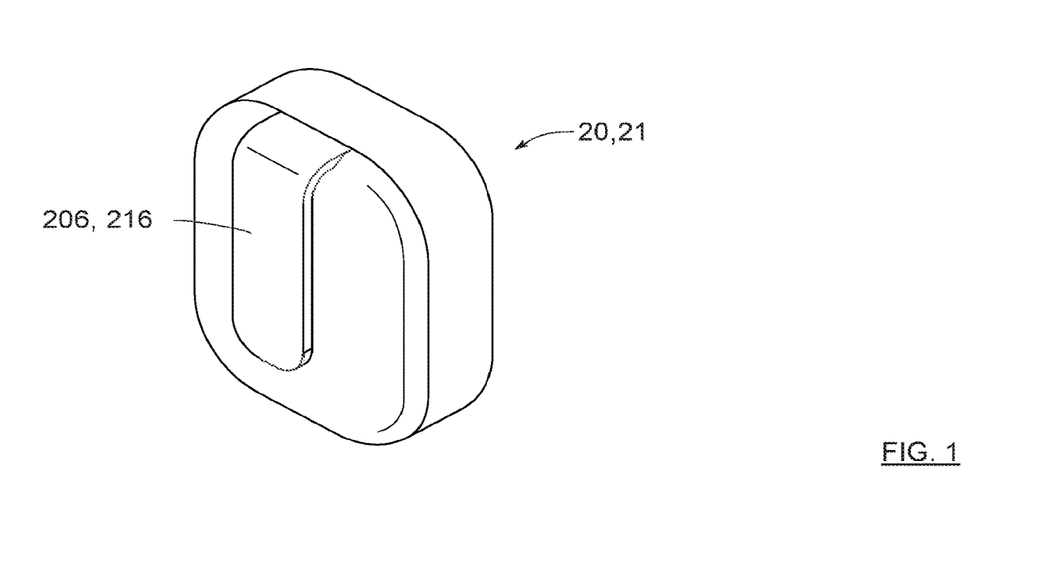
FIG. 1 illustrates measuring equipment according to an embodiment of the invention.
Figure 2:
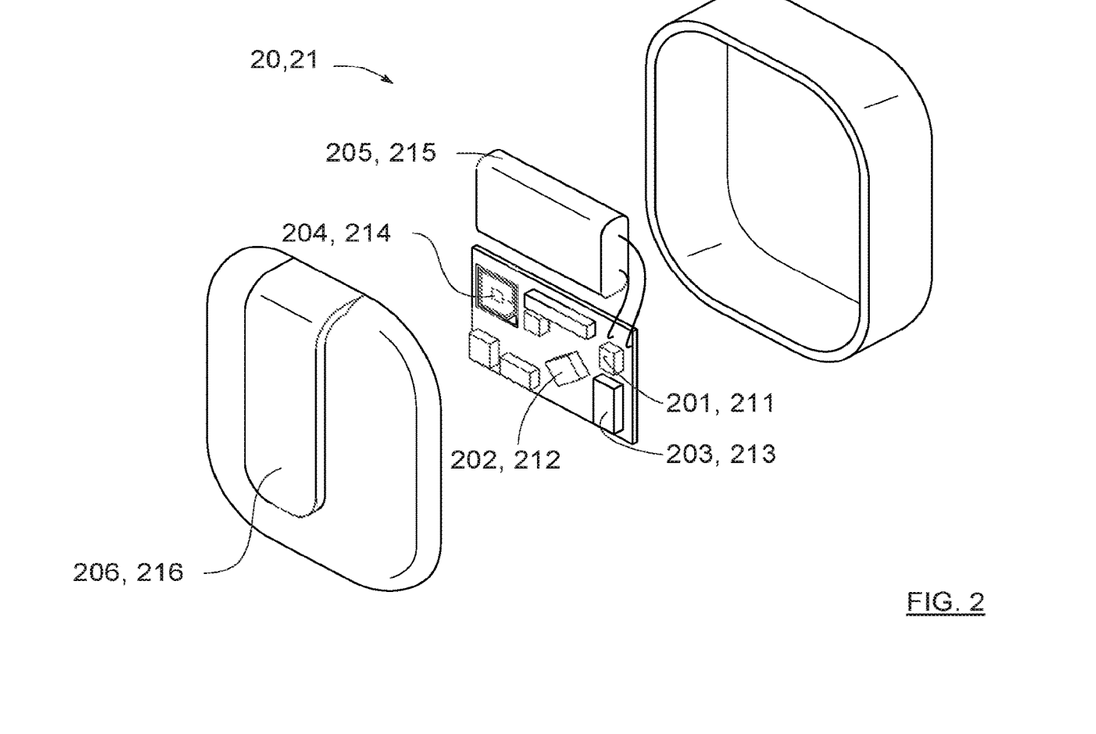
FIG. 2 illustrates the measuring equipment of FIG. 1, the housing of which is open in order to reveal the embedded electronic components thereof.

FIGS. 1 and 2 illustrate measuring equipment 20, 21 according to one embodiment of the invention. The measuring equipment as illustrated does not comprise a man-machine interface; it has none. The only thing that distinguishes the external appearance thereof from a simple box consists of a clip 206, 216 by means of which the measuring equipment can for example be worn removably on the belt of a user. The measuring element 20, 21 is not limited to the example illustrated in the figures. Though it is advantageously possible for it not to comprise a man-machine interface, in particular for reducing the cost thereof, it may also comprise one, even if only an on-off button, or one from among an LED, a screen, preferably electronic (or "e-paper") a vibrator, a piezoelectric loudspeaker, etc. It may comprise for example a scanner configured for example to read a QR code as a proximity beacon. It may be integrated in a bracelet (wrist or ankle), a boxing glove, a shoe, an oversock, a helmet, etc. It may be configured to be carried by a given part of the body or alternatively by a plurality of given parts of the body.

FIG. 2 illustrates more particularly the measuring equipment 20, 21, the housing of which is open in two parts so that its electronic components are visible. The measuring element 20, 21 may comprise at least:

- a means for measuring the performances, or sensor 201, 211, configured to measure at least one from among acceleration, a speed, an amplitude of movement, a number of revolutions per minute, a number of movements per minute and a type of movement, or even an energy/calories ratio. To do this, it may comprise at least one from among an accelerometer, preferably triaxial, which may be supplemented by at least one from among a gyroscope, preferably triaxial, and a magnetometer, preferably triaxial;
- a means for recognising the movements executed by the user (hook, uppercut, pump, squat, skipping rope, etc.) comprising a calculation unit 202, 212 (microcontroller or microprocessor), preferably low consumption, for processing in real time, in accordance with algorithms for movement recognition embedded in the calculation unit, at least the measurements supplied by the sensor or sensors 201, 211;
- a first radio-frequency communication means or transceiver 203, 213 for data in accordance with a communication technique having a longer range than a near-field communication technique and less long than a long-range communication technique, for example of the BTLE (standing for Bluetooth low energy), Xbee, Zigbee, Wi-Fi, etc. type, or in accordance with a long-range communication technique, preferably of the LoRa or Sigfox type;
- a second radio-frequency communication means 204, 214 in accordance with a near-field communication technique, for example of the NFC, RFID, etc. type, or an optical recognition means such as a QR code scanner, etc.;
- a memory support for storing data relating to the performances measured and/or to the movements recognised. This memory stores these data at least until they are transmitted;
- a battery 205, 215, preferably rechargeable by magnetic induction, for example in accordance with the Qi wireless recharge technology.

Figure 3:
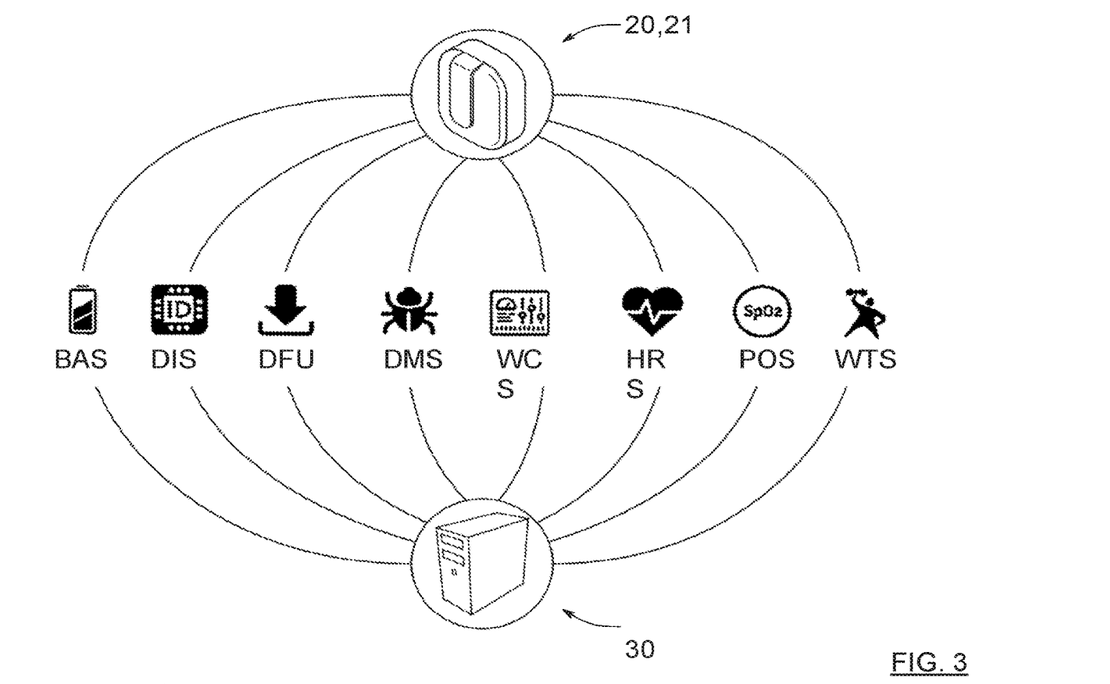
FIG. 3 illustrates a data-presentation method used between the measuring equipment of FIG. 1 and a communication node according to an embodiment of the invention.

FIG. 3 illustrates a way for the presentation of data used between the measuring equipment 20, 21 of FIG. 1 and a communication node 30 in accordance with one embodiment of the invention.

The communication node 30 comprises at least one means for pairing and receiving data. It may more particularly be a mobile communication device, for example of the smartphone or smartwatch type, a hub, a computer or a tablet. A hub may here be defined as an access point for simultaneously connecting a plurality of measuring equipment and to couple them and associate them with each other. The communication node 30 may also comprise a communication means, cabled or not, long range, such as an Internet connection, for the transfer of data to a local and/or distant database 40. The communication node 30 may be a personal computer (PC), a server or a nanocomputer, for example of the Raspberry type.

The data base 40 (illustrated in FIG. 4) may comprise a memory support configured to archive data supplied by the measuring equipment 20, 21 and/or by the communication node, locally and/or on a server. The database is preferably structured (user, sports hall, sporting activity, etc.).

One or each communication node 30 and/or a local or distant server connected to the database 40 may be configured to implement an installed software solution capable of aggregating and segmenting on multiple criteria the data supplied by the measuring equipment 20, 21 and/or by the communication node 30, respectively, or calculating other data according to the data supplied by the measuring equipment 20, 21 and/or by the communication node 30, respectively. Among the multiple criteria that said software solution may take into account, it is also possible to count data relating to the user, such as his size, weight and level of practice in various sporting activities. The software solution is thus advantageously able to take into account these data in order to adjust the requirement level and to decide to validate, and therefore to count or not a captured movement, for example an uppercut.

The presentation way illustrated in FIG. 3 is more particularly that of a BTLE profile, but is not limited thereto. FIG. 3 illustrates that the communication system 1 according to one embodiment of the invention integrates standard services such as the status of the battery, or BAS, which gives information on the charging level of the battery of the measuring equipment 20, 21, the service information of the device or DIS (standing for "device information service"), which gives information on the parameters relating to the measuring equipment (manufacturer, version, etc.), the heart rate service (HRS), the pulse oximeter service or POS, and others (DFS, standing for device firmware update, etc.). It also integrates personalised services, not forming part of a current standard, making it possible to perform the various types of interactive training described below. More particularly, the "Workout Control Service" or WCS integrates all the communication parameters, in particular with a view to identifying a sporting activity, the "Workout Training Service" or WTS integrates all the parameters for managing an interactive training, and the DMS service, standing for "Debug mode service".

Figure 4:
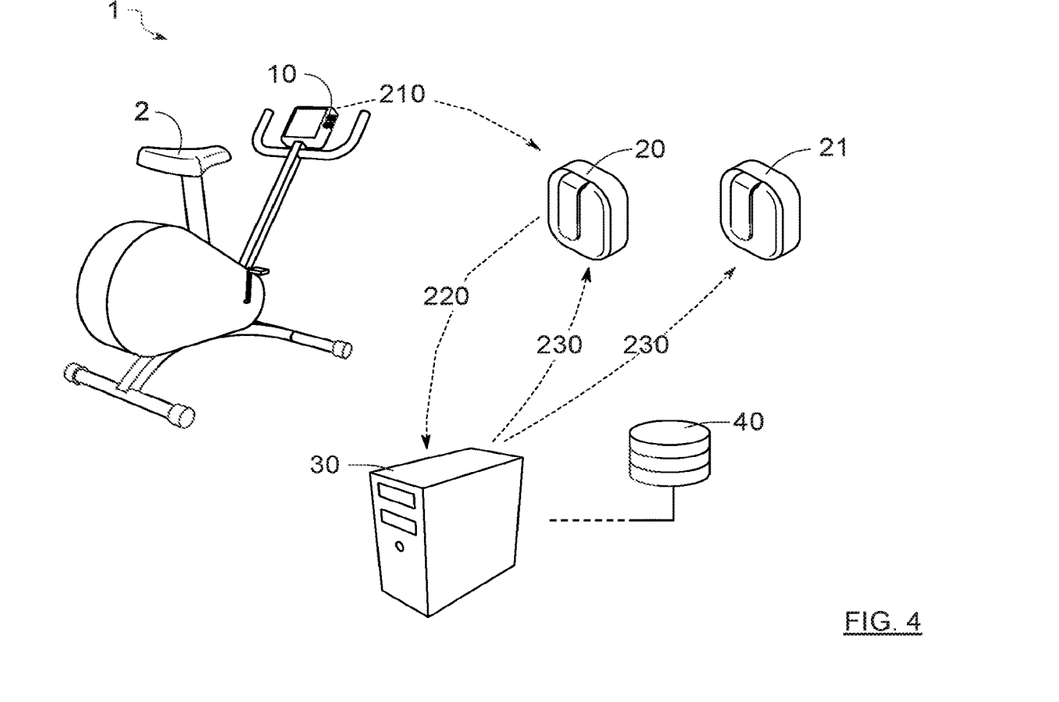
FIG. 4 illustrates a communication system according to an embodiment of the invention.

FIG. 4 illustrates a communication system according to one embodiment of the invention. The communication system 1 comprises at least: a proximity beacon 10, a measuring equipment 20, 21 intended to be worn by a user and configured to quantify at least one sporting activity of a user, and a communication node 30, as described above.

The communication system preferably comprises a plurality of measuring equipment 20, 21, each user being able to wear a plurality of measuring equipment and/or a plurality of users being able to have their physical activity or activities quantified at the same time by virtue of the present invention.

The communication system may comprise a plurality of communication nodes 30 distributed spatially so as to form a local area network. At least one communication node 30 may where applicable be configured to communicate in accordance with a long-range communication technique for example, with at least one from among a distant database 40 and another local area network formed by another plurality of communication nodes included in the communication system 1.

The communication system 1 may also comprise at least one communication device (not shown), chosen from at least one audio communication device, a visual communication device and an audiovisual communication device. Said communication device is configured to broadcast an information content, generated by the communication node 30, and potentially at the database 40, intended for at least one user. Said communication device may comprise a screen, a speaker, audio headphones, a smartphone, or a website, and allow sharing of the performances of users and other information of interest by means of social networks.

The proximity beacon is carried by a sports equipment 2, which is an indoor bicycle in the example illustrated. More generally, a proximity beacon is fixed to each sports equipment 2 via which a user may practice a sporting activity to be quantified. Each proximity beacon 10 is configured to store and can communicate, to measuring equipment 20, 21 or to a communication node, at least one identifier relating to a sporting activity associated with the sports equipment 2 to which it is fixed.

A plurality of measuring equipment may be necessary for the quantification of a sporting activity. For example, a symmetrical sporting activity, such as indoor bicycle, may require measuring equipment integrated in a bracelet and measuring equipment worn by an ankle of the user; the first makes it possible for example to measure the heart rate and the oxygen concentration in the blood of the user, while the second makes it possible for example to measure a number of revolutions per minute. For example, an asymmetrical sporting activity, such as boxing, may require more than two, or even five, measuring equipment; the first makes it possible for example to measure the heart rate and the oxygen concentration in the blood of the user, while the other four are each worn on a limb of the user in order to measure the movements of each of these limbs.

Before describing the sporting-activity quantification method 100 according to a preferred embodiment of the invention with reference to FIGS. 4 and 5, a contextualisation is described below by way of example in the case of application by deployment of the communication system 1 in a sports hall or a sports complex.

Initially, the user may be considered to be out of range of a communication node 30 equipping the sports hall and the measuring equipment 20, 21 worn by the user may be in a standby mode in which the sensors 201, 211 are stopped in order to save on the energy of the battery 205, 215. The measuring equipment are able to be known by the communication nodes so that the bringing by the user of said equipment 20, 21 into the coverage area of the communication node 30, for example by passing through a door of the sports hall, can cause the detection of the measuring equipment 20, 21 by the communication node 30. Following such detection, the communication node 30 can send a connection request to the measuring equipment 20, 21. In response to this connection request, the measuring equipment is activated. The connection is then established and the measuring equipment goes into connection mode.

Each measuring equipment 20, 21 comprising a clock can synchronise its clock with that of the communication node 30. This operation may relate solely to the communication protocol between each measuring equipment 20, 21 and the communication node 30. Alternatively, the synchronisation of the clock of each measuring equipment 20, 21 may follow a protocol for specifying the defined time specifically to the system 1 and for example included in the WCS service. This makes it possible to identify when the measurements have been made for the real-time applications.

Still at the stage following the activation of each measuring equipment 20, 21, the sensors 201, 211 preferably remain still stopped in order to save on the energy of the battery 205, 215, and this as long as the sporting activity has not begun. It is only once the sporting activity has been identified as detailed below that the sensors 201, 211 are activated so as to quantify the sporting activity.

Figure 5:
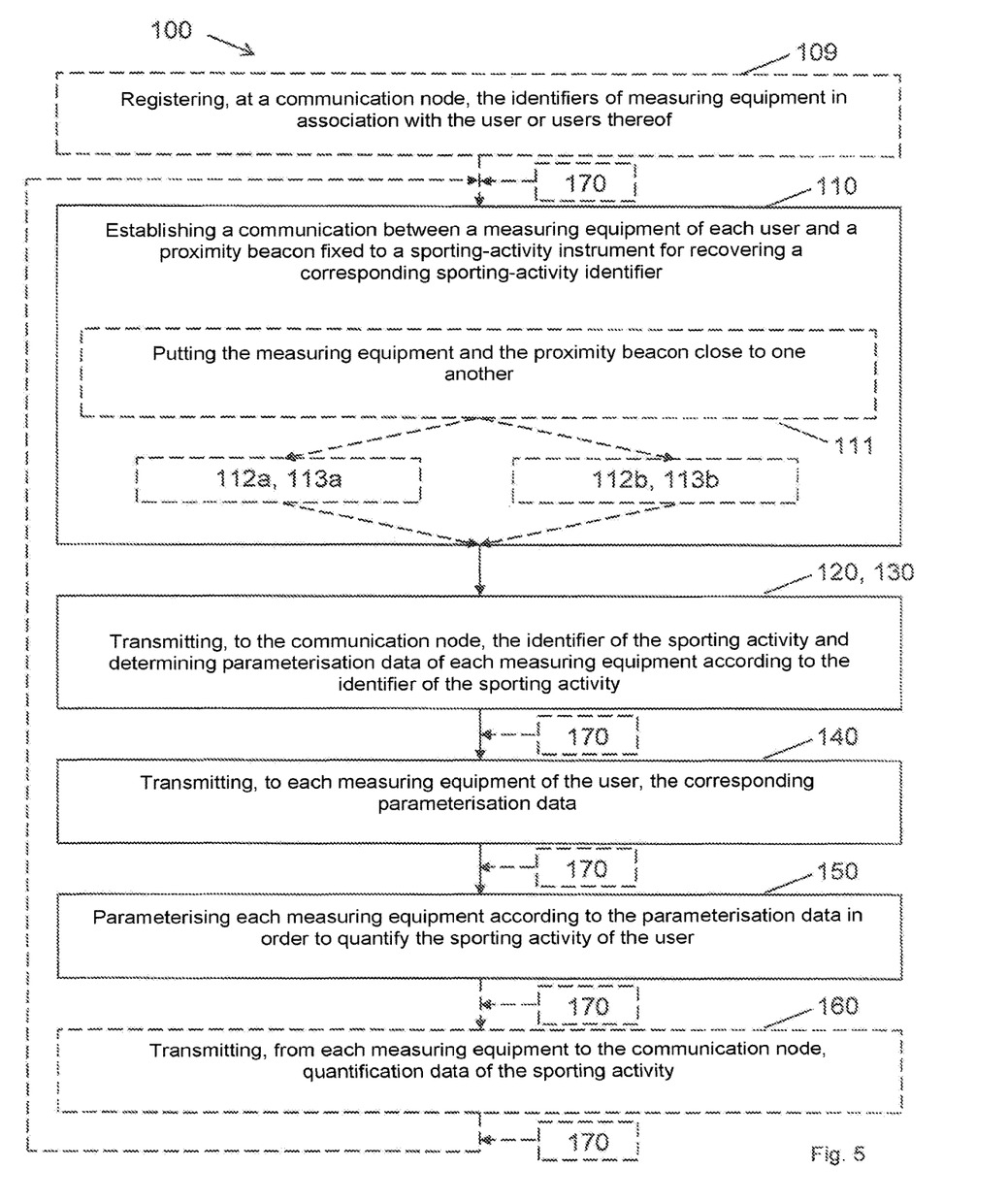
FIG. 5 is a flow diagram of the method for quantifying a sporting activity or activities according to an embodiment of the invention.

With reference to FIGS. 4 and 5, the sporting-activity quantification method 100 according to one embodiment of the invention is described below.

In the example illustrated in FIG. 4, the method 100 is implemented by a communication system 1 comprising a NFC module as a proximity beacon 10, a measuring equipment 20 equipped with a RFID chip reader and a hub as a communication node 30; the sports equipment 2 is an indoor bicycle. As detailed previously, the quantification of a sporting activity consisting of cycling may require two measuring equipment 20 and 21. The hub 30 is configured for example to communicate at least with measuring equipment 20, 21 by the BTLE (Bluetooth low energy) communication technique. The hub 30 may further be connected, for example via the Internet, to a local or distant database 40 that it can interrogate in order to recover data of interest. As an alternative or in addition, the hub 30 stores at least some of these data of interest and can determine them autonomously, without having to recover them from the database. One or more screens as communication devices are for example distributed in the sports hall at identified points so as to be able to communicate 170 with each user of the sports hall, in particular according to his location, either expected or determined (for example by a geolocation system, not described here) in the hall.

The method 100 may first of all comprise a step 109 of registration, at the hub 30, of the identifiers of the measuring equipment 20, 21. Alternatively, if the measuring equipment 20, 21 is already known to the hub as equipping the same user, these identifiers are already registered. Each identifier of the measuring equipment 20, 21 is therefore on this occasion or previously associated with the user, and more particularly with a user profile. The user profile may in particular comprise data relating to his size, his weight, his age, his level of practice (professional, amateur or beginner). These data can be taken into account in the processing of the measuring data, in particular in order to define, for example algorithmically, threshold values, optionally dependant on the sporting activity practised, of the requirement level for validating and counting the movements of the user.

Where applicable, each identifier of the measuring equipment 20, 21 is furthermore associated with at least one from among a mode of integrating the equipment and a mode of wearing the equipment, during this registration step.

This supplementary association is for example done by the user or an employee of the sports hall via a suitable hardware and software interface of the hub 30. Alternatively, each supplementary association may also be defined automatically by means of data stored in each measuring equipment 20, 21 and read by the hub 30. More particularly, these data stored in each measuring equipment 20, 21 may comprise a table of data, an input of which is the identifier of the measuring equipment and an output of which is data such as the manufacturer, the distributor, the version, the integration mode, the wearing mode planned, etc. The registration step 109 may thus be transparent for the user.

Each of these potential associations may also have been entered upstream by the user on a dedicated website, for example via his smartphone.

The registration step 109 is not necessarily renewed at each new implementation of the method 100. When measuring equipment 20, 21 is newly brought within range of a hub 30, the hub will be capable of finding the data and their potential associations with a user, a mode of wearing, etc.

At this stage, the hub 30 may for example be caused to communicate 170 with the user via the screen, for example so as to let him know that he is indeed registered as a wearer of the measuring equipment and which mode of wearing this measuring equipment is provided for in the databases.

As illustrated in FIGS. 4 and 5, the method comprises the following steps to quantify the sporting activity that the user wishes to practice.

A first step consists of communicating 110, from the NFC module 10 to the measuring equipment 20, a first data packet 210 comprising an identifier relating to a sporting activity associated with the sports equipment 2. The identifier relating to the sporting activity here relates to the practice of indoor cycling. Data other than the identifier relating to the sporting activity may be communicated by the first data packet 210, including for example the manufacturer, the version, the country or the club of installation, of the indoor bicycle 2.

According to another embodiment, the identifier relating to the sporting activity may in fact comprise only an identifier of the proximity beacon 10 with which there would have been associated, for example at the time of installation of the platform, a sporting activity, at the hub 30 or the database 40. In this embodiment, the identification of the activity will take place subsequently by means of a database that associates the identifier of the beacon with a sporting activity or which associates the identifier of the beacon directly with the parameterisation data of the measuring equipment.

The step 110 of communication between the measuring equipment 20 and the NFC module 10 may comprise more particularly:

the putting in proximity 111 of the measuring equipment 20 and the NFC module 10, the NFC module 10 being passive, the reading 112a by the measuring equipment 20 of the data stored in the NFC module 10, including at least the identifier of the sporting activity, and the transmission 113a, from the measuring equipment 20 to the communication node 30, of the first data packet 210, the first data packet 210 being able then to comprise, apart from the identifier relating to the sports equipment, the identifier of the measuring equipment 20.

A second step may consist of transmitting 120, from the measuring equipment 20 that communicated with the NFC module 10, to the hub 30, a second data packet 220 comprising the identifier of the sporting activity, and where applicable other data read on the NFC module or stored on the measuring equipment 20. Consequently, the hub 30 can communicate 170 with the user via the screen, for example so as to inform him which mode of wearing his measuring equipment 20, 21 is provided for in the databases in order to quantify the sporting activity identified. The user can thus be invited to equip one of his wrists with the measuring equipment 20 and one of his ankles with the measuring equipment 21.

A third step may consist, at the hub 30, of recovering 130 on at least one from among the database 40 and a storage medium of the hub 30, data for parameterising the measuring equipment 20, 21 according to the identifier of the sporting activity, and where applicable according to other data read on the NFC module or stored on the measuring equipment 20. Consequently, the hub 30 can communicate 170 with the user via the screen, for example so as to inform him which quantification parameters will be taken into account or to inform him which screen is provided in order to enable him to monitor his performances in real time or to inform him which real-time monitoring parameters will be displayed on said screen for his attention.

A fourth step may consist of transmitting 140, from the hub 30 and to each of the measuring equipment 20, 21, a third data packet 230 comprising at least the parameterisation data for each of the measuring equipment 20, 21. More particularly, a third data packet 230 comprising at least the parameterisation data for a first measuring equipment 20 may be transmitted 140 to the latter and a third data packet 230 comprising at least the parameterisation data for a second measuring equipment 21 may be transmitted 140 to the latter. The identifier of the second measuring equipment is known to the hub 30, for example either because the measuring equipment 30 can know the identifier of the second measuring equipment, or because the identifiers of the first and second measuring equipment have previously been associated during the registration 109. In this way, the hub 30 is actually in a position to transmit 140, to the second measuring equipment, its parameterisation data. Alternatively, the parameterisation data for the second measuring equipment are transmitted 140 to the first measuring equipment 20, which transmits them to the second. It should be noted here that only one measuring equipment 20 out of the two 20, 21 has to be able to communicate with the NFC module 10; the other one 21 of the two measuring equipment 20, 21 therefore does not necessarily comprise NFC communication means.

A fifth step may consist, at each measuring equipment 20, 21, of parameterising the measuring equipment according the parameterisation data that it has received and then quantifying 150 the sporting activity of the user by means of the measuring equipment 20, 21 parameterised according to said parameterisation data. At this stage, at least some of the sensors 201, 211 of the measuring equipment 20, 21 are activated.

The activation of the sensors 201, 211 may be performed immediately after the parameterising of each measuring equipment 20, 21 or be delayed. This delay in activation may be related to a predetermined waiting time (which may for example depend on the sporting activity identified: bicycle race with flying start). The delay in activation may also be related to a countdown communicated 170 to the user, for example displayed on the screen, or related to an action of a sports coach (for example, the coach manipulates his tablet or smartphone when all the practitioners are ready to begin the exercise).

In the case where each measuring equipment 20, 21 comprises a plurality of sensors 201, 211, the parameterising of each measuring equipment 20, 21 may comprise the activation of only some of the sensors 201, 211 in said plurality, according to the parameterisation data received. For example, if the first and second measuring equipment each comprise a heart-rate sensor and an accelerometer, it is possible that, out of the two heart-rate sensors, only that of the first measuring equipment 20 (worn on the wrist) is activated, and that, on the two accelerometers, only that of the second measuring equipment 21 (worn on the ankle) is activated. At this stage or prior to the firth stage, the hub 30 may still communicate 170 with the user via a screen, for example so as to recommend to him a posture to be adopted for virtual demonstrations of use of the sports equipment or to inform him that the quantification of the sporting activity will begin at the end of a countdown displayed.

Furthermore, during the quantification 150 of the sporting activity, any errors due to the uncertainties in transmission by the BLE technology (for example because of the distance and the orientation of the measuring apparatus, due to the projection, due to the H/S variability, etc.) between each measuring equipment 20, 21 and the communication node 30, can be eliminated by virtue of the synchronisation of their clocks. If the drift of the clocks of the measuring equipment 20, 21 is small, the synchronisation thereof can be effected only when the sensors 201, 211 are activated.

The quantification method 100 may further comprise, for example following or during the quantification 150 of the sporting activity, the transmission 160, from each measuring equipment 20, 21 to the communication node 30, of a fourth data packet comprising quantification data for the sporting activity. Preferably, the recognition of the movements and the calculation of the performances and physiological parameters are performed at at least one of the measuring equipment 20, 21. For example, the first measuring equipment 20 measures the heart rate of the user and the second measuring equipment 21 measures a number of revolutions per minute and where applicable a corresponding speed and/or acceleration. In this way only the results potentially resulting from a pre-processing of the measurements made by the sensors 201, 211 are transmitted 160 to the hub 30. Consequently the hub 30 can communicate 170 with the user via the screen, for example to enable him to follow his performances in real time.

As depicted in FIG. 5, the method 100 may be reiterated, for example when a first sporting activity is finalised, in order to begin a new sporting activity. A beacon 10 other than the one previously acted on may be read by the measuring equipment 20, etc. Alternatively, the same beacon 10 as the one previously acted on may be read by the measuring equipment 20. In this case, the beacon 10 will in the meantime have been reprogrammed in order to communicate 110 another identifier relating to another sporting activity, identifying the new sporting activity to be practised. This reprogramming may for example be performed by a sports coach via a communication node, for example of the smartphone or tablet type, for example in order to change from a "squat" activity to a "step" activity during fitness training. Alternatively or in addition, this reprogramming may again obey a pre-established program, for example of occupation of the sports hall:

from 6 pm to 8 pm, yoga class;
from 8 pm to 10 pm, fitness class; etc.

Thus the quantification method 100 according to the invention allows in particular:

a unified digital monitoring of all the physical activities offered in sports and/or fitness halls, and
a real-time quantification of the physical effort for interactive trainings.

The hardware and software platform offered enables users to train alone or in a group, on a machine or without a machine, at the same place or at a distance.

The possible applications are extremely numerous. To mention a few of them:

Interactive class: Training in a group with a coach and real-time quantification of the physical efforts made by each of the members of the group. The coach can define collective and individual objectives to be achieved (e.g.: number of calories burnt in the group, number of kicks given, etc.) in order to motivate the training session.

Training course: The users follows a training course dispensed by a virtual coach. The transfer to the communication node in real time of the data related to the physical effort enables the virtual coach to adapt the training (rate, intensity, duration, etc.).

Interactive studio: Training in front of a screen (or other) with quantification of the physical effort made by one or more users in real time. The results are displayed on a screen (or other) allowing monitoring and analysis of the effort during the session. These interactive studios allow "gamification" of the training. By way of example, the more a user trains, the more competitive the avatar associated with him becomes. Conversely, the competitiveness of the avatar regresses with lack of training by the user. The performances achieved by the avatar (the mirror of the user) make it possible to win more and more difficult challenges or the like with monetisation of the effort.

Air active challenge: The users can confront each other in the same sports hall or at a distance on sporting challenges (e.g. Air combat).

Active Game: Sporting puzzle to be solved in a team by achieving/exceeding sporting performance objective/threshold defined in a game scenario and measured in real time on the users.

In the light of the above detailed description, it is clear that the invention offers a particularly effective solution for providing the following advantages achieved separately or in combination:

Identification of the sporting activity practised,
Precise recognition of movements resulting from various sporting activities by the same measuring equipment or the same plurality of measuring equipment,
Improvement of the precision of quantification of the sporting activity practised,
Quantification and aggregation in real time of the physical activity of a plurality of users, and
Simplicity of use, in particular by the practitioners, but also by the coaches.

The invention is not limited to the embodiments described above and extends to all embodiments covered by the claims.

A first alternative would be to replace the NFC communication by an RFID communication and to follow the method 100 described above. In addition to this first alternative, the NFC module could be replaced by a QR code or a bar code; at least one measuring equipment 20 will then have to be equipped with a corresponding reader. For the rest, the method 100 is as described above.

A second alternative would be that the NFC module 10 is active. The method would then comprise, with reference to FIG. 5, the reading 112b by the NFC module 10 of data stored in the measuring equipment 20, including at least the identifier of the measuring equipment, and the transmission 113b, from the NFC module 10 to the communication node 30, of the first data packet 210, comprising at least the identifier of the sporting activity and the identifier of the measuring equipment.

Moreover, the communication node 30 may comprise a mobile telecommunication device, such as a smartphone, configured to communicate at least in accordance with a long-range communication technique. Thus the transmission 160 of the fourth data packet comprising the quantification data of the sporting activity can be done from said mobile communication device to at least one from among another communication node 30 and a distant database 40.

It should also be noted that the communication node may be associated with other sensors, in particular movement sensors, independent of the measuring equipment worn by a user in order to increase the precision of the measurements made and retrieval to the user. In particular, the invention is entirely compatible with the addition of a movement capture device such as touch tiles placed on the ground on which the user, during his sporting practice, presses in alternation, or devices for movement capture by video.

The invention claimed is:

1. A method for quantifying a sporting activity, the method being implemented by a communication system comprising at least: a proximity beacon carried by a sports object, measuring equipment intended to be worn by a user, the measuring equipment being configured to quantify at least one sporting activity of a user, and a communication node, the method comprising:

communicating between the measuring equipment and the proximity beacon, so as to recover a first data packet comprising at least one from an identifier relating to a sporting activity associated with the sports object and an identifier of the measuring equipment;

transmitting, from at least one from the measuring equipment and the proximity beacon, to the communication node, a second data packet comprising at least the identifier relating to the sporting activity and the identifier of the measuring equipment;

at the communication node, recovering parameterisation data of the measuring equipment to configure at least one sensor on the measuring equipment at least according to the identifier relating to the sporting activity, transmitting, from the communication node to the measuring equipment, a third data packet comprising at least said parameterisation data; and at the measuring equipment, parameterising the measuring equipment according to said parameterisation data and quantifying the sporting activity of the user of the measuring equipment parameterised according to said parameterisation data, wherein a plurality of measuring equipment is configured to be worn by the user and at least one from among the plurality of measuring equipment communicates with the proximity beacon, wherein the communication node further recovers different parameterisation data of each of the other measuring equipment in the plurality and wherein the communication node further transmits to each of the other measuring equipment in the plurality, a third data packet comprising at least parameterisation data of this measuring equipment, and the method further comprising transmitting, from each measuring equipment, to the communication node, a fourth data packet comprising quantification data of the sporting activity.

2. The method according to claim 1, wherein communicating between the measuring equipment and the proximity beacon comprises:

putting in proximity the measuring equipment and the proximity beacon, wherein the proximity beacon is passive, reading by the measuring equipment, in accordance with a near-field communication technique, of data stored in the beacon including at least the identifier relating to the sporting activity, and transmitting, from the measuring equipment to the communication node, the first data packet.

3. The method according to claim 1, wherein, for each of the measuring equipment in the plurality, the parameterisation data of the measuring equipment are further recovered according to an identifier of this measuring equipment.

4. The method according to claim 1, wherein, each measuring equipment being associated with a unique identifier, the identifier of each of said other measuring equipment is recovered by the communication node according to an identifier of the measuring equipment that communicated with the proximity beacon.

5. The method according to claim 1, wherein the method further comprises, before communicating between the measuring equipment and the proximity beacon, at the communication node:

registering, by associating them, the identifiers of the measuring equipment forming part of a same plurality associated with one from among a user and a plurality of users intended to practice the same sporting activity.

6. The method according to claim 5, wherein the sports object is or comprises a sports hall and wherein the beacon is carried by a terminal of the sports hall.

7. The method according to claim 1, wherein the method further comprises, before communicating between the measuring equipment and the proximity beacon, at the communication node: registering in advance an association of the identifier of the measuring equipment and user data.

8. The method according to claim 1, wherein the communication system comprises a plurality of communication nodes distributed spatially so as to form a local network.

9. The method according to claim 8, wherein at least one communication node in the plurality is configured to communicate with at least one from among a distant database and another local network formed by another plurality of communication nodes included in the communication system.

10. The method according to claim 1, wherein the plurality of measuring equipment comprises a respective plurality of sensors and wherein parameterising of the plurality of measuring equipment according to the different parameterisation data comprises at least the activation of at least one sensor in said plurality of sensors and deactivation of at least one sensor in another of said plurality of sensors.

11. The method according to claim 1, wherein the measuring equipment comprises at least one accelerometer, and wherein the quantification of the sporting activity comprises at least one step of measuring at least one of: an acceleration, a speed, a movement amplitude, a number of revolutions per minute, a number of movements per minute, a number of repetitions of movement(s) and a movement type.

12. The method according to claim 1, wherein the communication node comprises a mobile telecommunication device, and wherein transmitting the fourth data packet comprises transmitting from said mobile communication device to at least one from among another communication node and a distant database.

13. The method according to claim 1, wherein each measuring equipment is synchronised with a clock of a communication node.

14. The method according to claim 1, wherein a single measuring equipment from among a plurality of measuring equipment communicates with the proximity beacon, wherein the communication node further recovers parameterisation data of each of the other measuring equipment in the plurality of measuring equipment; and wherein the communication node further transmits to each of the plurality of measuring equipment other than the single measuring equipment, a third data packet comprising at least parameterisation data of this measuring equipment.

15. The method according to claim 1, wherein the measuring equipment comprises at least one triaxial accelerometer, and
wherein the quantification of the sporting activity comprises at least one step of measuring at least one of: an acceleration, a speed, a movement amplitude, a number of revolutions per minute, a number of movements per minute, a number of repetitions of movement(s) and a movement type.

16. The method according to claim 1, wherein the measuring equipment comprises at least one of a triaxial gyroscope and a triaxial magnetometer.

17. A method for quantifying a sporting activity, the method being implemented by a communication system comprising at least: a proximity beacon carried by a sports object, measuring equipment intended to be worn by a user, the measuring equipment being configured to quantify at least one sporting activity of a user, and a communication node, the method comprising:
communicating between the measuring equipment and the proximity beacon, so as to recover a first data packet comprising at least one from an identifier relating to a sporting activity associated with the sports object and an identifier of the measuring equipment;
transmitting, from at least one from the measuring equipment and the proximity beacon, to the communication node, a second data packet comprising at least the identifier relating to the sporting activity and the identifier of the measuring equipment;
at the communication node, recovering parameterisation data of the measuring equipment to configure at least one sensor on the measuring equipment at least according to the identifier relating to the sporting activity,
transmitting, from the communication node to the measuring equipment, a third data packet comprising at least said parameterisation data; and
at the measuring equipment, parameterising the measuring equipment according to said parameterisation data and quantifying the sporting activity of the user of the measuring equipment parameterised according to said parameterisation data,
wherein a plurality of measuring equipment is configured to be worn by the user and at least one from among the plurality of measuring equipment communicates with the proximity beacon, wherein the communication node further recovers different parameterisation data of each of the other measuring equipment in the plurality and wherein the communication node further transmits to each of the other measuring equipment in the plurality, a third data packet comprising at least parameterisation data of this measuring equipment, wherein the communication system further comprises at least one communication device, chosen from among at least one audio communication device, a visual communication device and an audiovisual communication device, for communicating an information content generated by the communication node, and wherein the method further comprises the communication of said information content to at least one user via said at least one communication device.

18. A non-transient medium that can be read by a computer, comprising instructions which, when they are executed by at least one processor, implement the method for quantifying a sporting activity according to claim 1.

19. A method for quantifying a sporting activity, the method being implemented by a communication system comprising at least: a proximity beacon carried by a sports object, measuring equipment intended to be worn by a user, the measuring equipment being configured to quantify at least one sporting activity of a user, and a communication node, the method comprising:
communicating between the measuring equipment and the proximity beacon, so as to recover a first data packet comprising at least one from an identifier relating to a sporting activity associated with the sports object and an identifier of the measuring equipment;
transmitting, from at least one from the measuring equipment and the proximity beacon, to the communication node, a second data packet comprising at least the identifier relating to the sporting activity and the identifier of the measuring equipment;
at the communication node, recovering parameterisation data of the measuring equipment at least according to the identifier relating to the sporting activity,
transmitting, from the communication node to the measuring equipment, a third data packet comprising at least said parameterisation data; and
at the measuring equipment, parameterising the measuring equipment according to said parameterisation data and quantifying the sporting activity of the user of the measuring equipment parameterised according to said parameterisation data,
wherein the method further comprises, before communicating between the measuring equipment and the proximity beacon, at the communication node: registering in advance an association of the identifier of the measuring equipment and user data.

* * * * *